United States Patent [19]
Haas et al.

[11] Patent Number: 5,714,347
[45] Date of Patent: Feb. 3, 1998

[54] PREPARATION OF RECOMBINANT UBIQUITIN CROSS-REACTIVE PROTEIN (UCRP) WITH IMPROVED BIOACTIVITY

[75] Inventors: Arthur L. Haas, Brookfield; Jana Narasimhan, Wauwatosa, both of Wis.

[73] Assignee: MCW Research Foundation, Milwaukee, Wis.

[21] Appl. No.: 577,640

[22] Filed: Dec. 22, 1995

[51] Int. Cl.$^6$ .......................... C12N 15/12; C07K 14/47
[52] U.S. Cl. .......................... 435/69.1; 530/350; 530/412
[58] Field of Search .......................... 435/69.1; 530/350, 530/412

[56] References Cited

U.S. PATENT DOCUMENTS

| | | | |
|---|---|---|---|
| 4,828,990 | 5/1989 | Higashi et al. | 435/68 |
| 5,418,192 | 5/1995 | Borden et al. | 435/69.51 |

OTHER PUBLICATIONS

Haas, et al., J. Biol. Chem., vol. 260(8): pp. 4694-4703 (1985).

P. B. Ahrens, et al., "Tumor necrosis factor enhances induction by β-interferon of a ubiquitin cross-reactive protein," J. Gen. Vir. 71:1675–1682, 1990.

K. J. Austin, et al., "Ubiquitin Cross-Reactive Protein is released by the Bovine Uterus in Response to Interferon during Early Pregnancy," Biol. of Reprod.54:600–606, 1996.

D. C. Blomstrom, et al., "Molecular Characterization of the Interferon–induced 15–kDa protein." J. Biol. Chem.261(19):8811–8816, 1986.

J. D'Cunha, et al., "Immunoregulatory properties of ISG15, and interferon-induced cytokine." Proc. Natl. Acad. Sci. USA93:211–215, 1996.

P. J. Farrell, et al., "Accumulation of an mRNA and protein in interferon-treated Ehrlich ascites tumour cells," Nature279:523–525, 1979.

N. Feltham, et al., "A 15–kD Interferon–Induced Protein and its 17–kD precursor: Expression in Escherichia Coli, Purification, and Characterization." J. Interfer. Res.9: 493–507, 1989.

A. L. Haas, et al., "Interferon Induces a 15–Kilodalton protein exhibiting Marked Homology to Ubiquitin." J. biol. Chem.262(23):11315–11323, 1987.

E. Knight, Jr., et al., "A 15–kDa Interferon–induced Protein is derived by COOH–terminal Processing of a 17–kDa Precursor," J. Biol. Chem. 263(10):4520–4522, 1988.

E. Knight, Jr., et al., "IFN–induced 15–kDa Protein is Released from Human Lymphocytes and Monocytes," J. Immun. 146(7):2280–2284, 1991.

B. D. Koran, et al., "Interferon–induced Proteins." J. Biol. Chem. 259(23):14835–14839, 1984.

K. R. Loeb, et al., "The Interferon–inducible 15–kDa Ubiquitin Homolog Conjugates to Intracellular Proteins," J. Biol. Chem. 267(11):7806–7813,1992.

J. Lowe, et al., "Immunohistochemical Localization of Ubiquitin Cross-Reactive Protein in Human Tissues." J. Pathol. 177:163–169, 1995.

J. Narasimhan, et al., "Conjugation of the 15–kda Interferon–induced Ubiquitin Homolog is Distinct from That of Ubiquitin." J. Biol. Chem.271(1):324–330, 1996.

J. Narasimhan, et al., "Conjugation of UCRP (ISG15) to Cellular Proteins," American Society for Biochemistry and Molecular Biology, San Francisco, California, May 21–25, 1995 (Abstract).

M. Recht, et al., "A Human 15–kDa IFN–Induced Protein Induces the Secretion of IFN–γ," 147(8):2617–2623, 1991.

N. Reich, et al., "Interferon–induced transcription of a gene encoding a 15–kDa protein depends on an upstream enhancer element," Proc. Natl. Acad. Sci. USA 84:6394–6398, 1987.

Loeb et al. J. Biol. Chem. vol. 267 (11) pp. 7806–7813 1992.
Haas et al. J. Biol. Chem. vol. 257 (17) pp. 10329–10337 (1982).
Haas et al. J. Biol. Chem. vol. 260 (8) pp. 4694–4703 (1985).

*Primary Examiner*—Stephen Walsh
*Assistant Examiner*—Daryl A. Basham
*Attorney, Agent, or Firm*—Quarles & Brady

[57] ABSTRACT

A method of preparing recombinant ubiquitin cross-reactive protein (UCRP) is disclosed. In one embodiment, the method comprises the step of purifying UCRP from a host cell in the presence of a cobalt or Group IIb metal, wherein the cobalt or Group IIb metal prevents proteolytic inactivation of UCRP occurring by cleavage of the UCRP carboxyl terminal glycine dipeptide. In another embodiment the method comprises purifying UCRP comprising an additional arginine or lysine residue at the carboxy terminal. A preparation of UCRP with an additional arginine residue at the carboxy terminus is also disclosed.

10 Claims, No Drawings

PREPARATION OF RECOMBINANT UBIQUITIN CROSS-REACTIVE PROTEIN (UCRP) WITH IMPROVED BIOACTIVITY

FIELD OF THE INVENTION

The field of the present invention is production of bioactive recombinant ubiquitin cross-reactive protein (UCRP). Specifically, the field of the present invention is production of a recombinant UCRP preparation in a manner that inhibits proteolytic inactivation of UCRP occurring by cleavage of the UCRP carboxyl terminal glycine dipeptide.

BACKGROUND

The interferons exert their biological effects through induction of a subset of cellular genes whose patterns of expression define the cell-specific and tissue-specific responses characteristic of these cytokines. Several of these interferon-induced genes have been the subject of considerable study (reviewed in Sen, G. C. and Lengyel, P. *J. Biol. Chem.* 267:5017–5020, 1992); however, the mechanisms by which many of these proteins contribute to the interferon response remain poorly understood.

One such protein within the latter group is the 15 kDa polypeptide originally identified by Farrell, et al. (Farrell, P. J., et al. *Nature* 279:523–525, 1979) and later characterized by Knight and coworkers (Blomstrom, D.C., et al. *J. Biol. Chem.* 261:8811–8816, 1986; Knight, E., Jr., et al. *J. Biol. Chem.* 263:4520–4522, 1988). Interferon-induced expression of the 15 kDa protein is regulated by an upstream interferon stimulated response element (ISRE) typical of all early genes induced by type 1 interferons, IFNα and IFNβ (Reich, N., et al. *Proc. Natl. Acad. Sci. USA* 84:6394–6398, 1987).

Subsequently, the sequence of the 15 kDa protein was noted to possess significant homology to a tandem diubiquitin sequence, accounting for its cross-reaction with affinity-purified anti-ubiquitin antibodies (Haas, A. L., et al., *J. Biol. Chem.* 262:11315–11323, 1987). The carboxyl terminal LRLRGG sequence of ubiquitin essential for its conjugation to cellular proteins is conserved within the carboxyl terminus of the Ubiquitin Cross Reactive Protein (UCRP), leading to the proposal that UCRP contributes to the type 1 interferon response through an analogous conjugation reaction (Haas, A. L., et al., supra, 1987).

More recently, high molecular weight UCRP conjugates have been detected constitutively and within interferon-induced cultured cell lines using anti-UCRP specific antibodies (Loeb, K. R. and Haas, A. L. *J. Biol. Chem.* 267:7806–7813, 1992; Loeb, K. R. and Haas, A. L. *Mol. Cell. Biol.* 14:8408–8419, 1994).

UCRP is the subject of U.S. Pat. No. 5,418,192 in which UCRP-mediated production of interferon gamma in mammalian CD3+ T-cells is described. In U.S. Pat. No. 5,418, 192, UCRP is termed "DA15" protein.

U.S. Ser. No. 08/329,911, filed Oct. 26, 1994, refers to UCRP as "IL-16" and describes the proliferative effect of UCRP on NK/LAK cells.

Ubiquitin is one of the most highly conserved proteins found widely distributed among eucaryotes. The best-studied function of ubiquitin is to target cellular proteins for degradation through a post-translational modification wherein the carboxyl terminus of ubiquitin is covalently linked via isopeptide bond to primary amines on target proteins (Hershko, A., et al., *Proc. Natl. Acad. Sci. USA* 77:1783–1786, 1980). The resulting conjugates are degraded by a multi-enzyme ATP-dependent pathway requiring the 26S multicatalytic protease complex (proteasome) (Hershko, A. and Ciechanover, A. *Ann. Rev. Biochem.* 61:761–807, 1992). Conjugation of ubiquitin to cellular proteins proceeds through a three-step pathway, reviewed in (Hershko, A. and Ciechanover, A., supra, 1992; Pickart, C. M. in *Ubiquitin* (Rechsteiner, M., ed) pp. 77–99, Plenum Press, New York, N.Y., 1988). The ubiquitin activating enzyme (E1) catalyzes an ATP-coupled activation of the carboxyl terminal glycine of ubiquitin to generate an enzyme-bound ubiquitin adenylate intermediate and free $PP_i$ (Haas, A. L. and Rose, I. A. *J. Biol. Chem.* 257:10329–10337, 1982). Transfer of activated ubiquitin to an active site cysteine of E1 releases AMP and generates a covalent E1-ubiquitin thiolester (Haas, A. L. and Rose, I. A., Supra, 1982). In the second step, ubiquitin is transferred by transacylation to a cysteine residue conserved among all members of a family of ubiquitin carrier proteins, E2 (Pickart, C. M. and Rose, I. A., *J. Biol. Chem.* 260:1573–1581, 1985; Haas, A. L. and Bright, P. M., *J. Biol. Chem.* 263:13258–13267, 1988). The third step involves aminolysis of these E2 thiolesters to form isopeptide bonds between the carboxyl terminal glycine of ubiquitin and ε-amino groups of lysine residues on target proteins in both E3 (ubiquitin:protein ligase) -dependent and -independent mechanisms (Haas, A., et al., *J. Biol. Chem.* 265:21664–21669, 1990).

What is needed in the art of protein purification is a preparation of UCRP with improved bioactivity.

SUMMARY OF THE INVENTION

The present invention is a method of preparing recombinant ubiquitin cross-reactive protein (UCRP) with improved bioactivity. In one embodiment, the method comprises the step of purifying recombinant UCRP from a host cell in the presence of cobalt or a Group IIb metal, wherein cobalt or the Group IIb metal prevents proteolytic inactivation of UCRP occurring by cleavage of the UCRP carboxyl terminal glycine dipeptide. In another embodiment, the method comprises the step of purifying recombinant UCRP wherein an additional arginine or lysine residue has been added to the carboxyl terminal of the UCRP molecule.

In a preferred form of the first embodiment of the present invention, the metal is cobalt, most preferably in the form of invention, the metal is cobalt, most preferably in the form of $CoCl_2$. The concentration of $CoCl_2$ is preferably between 3 mM and 10 mM, most preferably approximately 5 mM.

The method of the present invention may additionally comprise the step of analyzing the purified UCRP by measuring E1-catalyzed ATP:$PP_i$ exchange.

The method of the present invention may also additionally comprise the step of analyzing the purified UCRP by examining the UCRP directly to determine whether the carboxyl terminal glycine dipeptide is present. This examination may preferably be done by exposing the UCRP preparation to carboxypeptidase B and determining whether a pI shift has occurred.

In a preferred form the second embodiment of the present invention, the added residue is arginine and is subsequently removed with a peptidase, such as carboxy-peptidase B, after the protein has been purified.

The present invention is also a purified preparation of UCRP wherein the UCRP comprises UCRP with an additional arginine residue added to the carboxy terminal.

It is an object of the present invention to provide a preparation of UCRP with improved bioactive characteristics.

It is another object of the present invention to provide a preparation of UCRP in which the carboxyl terminal glycine dipeptide is intact.

Other objects, features and advantages of the present invention will become apparent by review of the specification and claims.

DESCRIPTION OF THE INVENTION

1. In General

Our goal was to provide a UCRP preparation with enhanced bioactive characteristics. By "enhanced" we mean that the recombinant preparation is equivalent to a native UCRP preparation in activity measurements. The present invention describes two methods to create a UCRP with an intact carboxyl terminal glycine dipeptide which we believe is necessary for bioactivity.

We have found that inclusion of $CoCl_2$ during the purification of recombinant UCRP blocks the proteolytic inactivation of the UCRP polypeptide that occurs by cleavage of the carboxyl terminal glycine dipeptide required for activation and subsequent ligation. Intact, bioactive UCRP supports a low rate of ubiquitin activating enzyme (E1)-dependent $ATP:PP_i$ exchange. In an in vitro conjugation assay, intact, bioactive $^{125}$I-UCRP could be ligated in an ATP-dependent reaction to proteins present within an A549 human lung carcinoma cell extract and could be competitively inhibited by excess unlabeled UCRP, but not by ubiquitin.

Therefore, the present invention is method of creating a recombinant UCRP preparation by including cobalt or a Group IIb metal in the protein preparation. Most preferably, the metal is cobalt. The bioactive properties of the protein preparation is typically measured by E1-dependent $ATP:PP_i$ exchange.

We have also found that inclusion of a carboxyl terminal arginine in an UCRP preparation inhibits proteolytic cleavage. The bioactive properties of this protein preparation are also typically measured by E1-dependent $ATP:PP_i$ exchange.

2. Integrity of the UCRP Carboxyl Terminus

Previously we had been unable to demonstrate conjugation of recombinant $^{125}$I-UCRP when added to fresh extracts of A549 cells (Loeb, K. R. and Haas, A. L. *J. Biol. Chem.*, supra, 1992; Loeb, K. R., supra, 1993). In addition, previous preparations of recombinant UCRP failed to support E1-catalyzed $ATP:PP_i$ exchange (Loeb, K. R. and Haas, A. L. *J. Biol. Chem.*, supra, 1992; Loeb, K. R., supra, 1993) in spite of the marked homology between UCRP and ubiquitin. The latter negative result suggested that either E1 was incapable of interacting with UCRP or that the recombinant protein was isolated in an inactive form. Our subsequent experiments have confirmed that recombinant UCRP isolated as described previously (Loeb, K. R. and Haas, A. L., supra, 1992) was at least partially inactive due to proteolytic cleavage of the carboxyl terminal glycine dipeptide.

Mature forms of ubiquitin and UCRP share a common LRLRGG carboxyl terminus (Haas, A. L., et al., supra, 1987). Previous work has shown that the carboxyl terminal glycine dipeptide of ubiquitin is acutely sensitive to cleavage by trypsin-like activities (Haas, A. L., et al., *J. Biol. Chem.* 260:4694–4703, 1985; Wilkinson, K. D. and Audhya, T. K., *J. Biol. Chem.* 256:9235–9241, 1981). The resulting des-glygly ubiquitin retains a pI characteristic of native ubiquitin (Haas, A. L., et al., supra, 1985; Wilkinson, K. D. and Audhya, T. K., supra, 1981). However, removal of the carboxyl terminal glycine dipeptide exposes R74 which is subject to cleavage by carboxypeptidase B to yield a product exhibiting a pI shift to 5.4 (Haas, A. L., et al., supra, 1985; Wilkinson, K. D. and Audhya, T. K., supra, 1981). The specificity of carboxypeptidase B for lysine and arginine precludes a similar pI shift for intact ubiquitin in which R74 is masked by the glycine dipeptide (Haas, A. L., et al., supra, 1985). When a similar experiment was conducted with recombinant UCRP isolated by the Haas, A. L., et al., supra, 1985 protocol, the polypeptide exhibited a shift in pI from the value of 6.7 characteristic of UCRP to 5.4 upon incubation with carboxypeptidase B. This indicated to us that the carboxyl terminal glycine dipeptide was absent from UCRP.

The pI shift upon incubation of ubiquitin with carboxypeptidase B was used as a convenient assay to test for carboxyl terminal glycine dipeptide processing in *E. coli* BL21 (DE3) extracts. These experiments revealed that the inactivating enzyme was a periplasmic carboxypeptidase similar in specificity to carboxypeptidase A; that is, the activity readily cleaved the glycine dipeptide from ubiquitin but failed to remove the resulting R74 carboxyl terminus. Similar inactivating activity was found in all expression strains of *E. coli* tested, except for that of AR58 used in the heat-inducible expression of recombinant ubiquitin (Burch, T. J. and Haas, A. L., *Biochemistry* 33:7300–7308, 1994). However, the AR58 expression system was precluded for UCRP since the polypeptide fails to fold into a soluble, native conformation at the elevated temperature (42° C.) required for induction (Loeb, K. R., supra, 1993).

Various inhibitors were unsuccessfully screened for their ability to block ubiquitin carboxyl terminal inactivation by BL21 extracts. In contrast, 5 mM EDTA stimulated the rate of ubiquitin inactivation, suggesting that endogenous divalent metal(s) present in the lysates acted as natural inhibitors of the activity.

We tested a variety of metal salts for the ability to inhibit ubiquitin inactivation. Among the metal salts subsequently tested, $CoCl_2$ was the most effective in inhibiting ubiquitin inactivation. Therefore, 5 mM $CoCl_2$ was included in all buffers used in the isolation of recombinant UCRP in the Examples, below, because this concentration quantitatively blocks ubiquitin and UCRP glycine dipeptide excision.

Other metal salts besides $CoCl_2$ are suitable for the present invention. In particular, $HgCl_2$ and $CdCl_2$ have been shown to be effective in inhibiting UCRP inactivation. In general, Group IIb metals and cobalt are useful in the present invention.

Most preferably, 3 mM to 10 mM metal salt is suitable for the present invention. Preferably, approximately 5 mM metal salt is used in the present invention.

Recombinant UCRP purified in the presence of $CoCl_2$ failed to show a pI shift upon incubation with carboxypeptidase B, suggesting the presence of an intact native carboxyl terminus. However, the pI of UCRP shifted from 6.7 to 5.4 following successive incubation with carboxypeptidase A, to remove the glycine dipeptide, followed by carboxypeptidase B. This latter control experiment precluded the possibility that residual $CoCl_2$ present in the UCRP preparation directly inhibited the activity of carboxypeptidase B.

3. Isolation of UCRP

The present invention is the preparation of UCRP that has not been subject to carboxyl terminal inactivation. Most preferably, the recombinant UCRP is prepared as described below in the Examples by propagation of *E. coli* BL21(DE3) harboring the pETUCRP expression plasmid. This expression plasmid can be obtained from the American Type Culture Collection, Rockville, Md., at accession number ATCC 68216.

The bacterial preparation is grown to a desired $OD_{600NM}$ (preferably 0.80D) and then harvested. Preferably, this harvest is after a 90 minutes incubation in the presence of 0.4 mM IPTG.

After this point, the present invention requires that recombinant UCRP be purified in the presence of the metal salt. "In the presence" means that both during the lysis of the host cell and during the subsequent stages of protein purification, the enzyme is always in the presence of at least 3 mM of the metal salt until the protein has been purified. The Examples below demonstrate an especially preferred purification wherein the enzyme is always in the presence of 5 mM $CoCl_2$.

The Examples below also disclose a preferred purification protocol. The centrifuged cells are resuspended in 50 mM TRIS-CL (pH 7.5) containing 5 mM $CoCl_2$ and lysed by French press. The preferred method of extracting UCRP is modified from the procedure of Loeb and Haas, 1992 (*J. Biol. Chem.* 267:7806–7813, 1992) which is incorporated by reference as if set forth herein. The Examples detail some specific changes from the Loeb and Haas procedure that are thought to be preferable.

4. Preparation of UCRP-R or UCRP-K

The present invention is also a method of preparing a bioactive recombinant UCRP preparation that requires the addition of an arginine or lysine residue to the carboxyl terminal. This additional arginine or lysine is most easily added by manipulating a UCRP clone to contain an additional arginine or lysine codon. The Examples below describe the modification of pETUCRP to encode an additional arginine residue at the carboxy terminus of the protein.

After the UCRP-R or UCRP-K preparation has been purified substantially from the host cell, one may remove the additional arginine or lysine residue with carboxypeptidase B, thus providing a UCRP molecule that more closely resembles the native molecule.

The bioactivity measurement of this UCRP preparation is identical to that described above and below for the metal-purified UCRP.

5. Determination of UCRP Bioactivity

Once one has obtained a preparation of UCRP, one will wish to determine whether the preparation is bioactive. By "bioactive" we mean intact UCRP containing the carboxyl terminal glycine dipeptide exposed on precursor processing of the naturally-occurring proprotein. A bioactive UCRP preparation will have essentially similar bioactivity to a native UCRP preparation.

The Examples below describe different activity assays. The first assay determines whether the preparation of UCRP supports E1-catalyzed $ATP:PP_i$ exchange. For a preparation to be bioactive the preparation must have the following characteristics: The preparation must be capable of supporting the E1-catalyzed $ATP:PP_i$ exchange reaction as evidence for the presence of the carboxyl terminal glycine dipeptide. Moreover, for complete bioactivity the preparation must be capable of supporting the E1-catalyzed $ATP:PP_i$ exchange reaction with a $K_{1/2}=24$ µM representing that of pure intact native UCRP (Narasimhan, et al., *J. Biol. Chem.* 271[1], 1996, in press) in which $K_{1/2}$ is defined as the concentration of UCRP yielding an initial velocity of $ATP:PP_i$ exchange equal to 50% of the maximal initial rate at saturating UCRP. A $K_{1/2}$ of 24 µM signifies that the purified UCRP preparation quantitatively contains an intact carboxyl terminus and that the protein bears a native protein conformation.

Another assay of the bioactive nature of the UCRP preparation is to determine whether incubation with carboxypeptidase B induces a shift in pI, as described above in the description of the integrity of the UCRP carboxyl terminal. Recombinant UCRP purified in the presence of $CoCl_2$ will fail to show a pI shift after incubation with carboxypeptidase B.

The pI shift is defined by the transfer of UCRP protein mass from a pI (Isoelectric point) of 6.7 to 5.4 following the proteolytic action of carboxypeptidase B in cleaving any UCRP molecules not containing a carboxyl terminal glycine dipeptide which prevents the action of carboxypeptidase B and prevents a shift in pI. The pI shift is measured by subjecting pure UCRP and carboxypeptidase B-treated UCRP to analysis on an isoelectric focusing gel of appropriate pH range (3.5–9.5). Quantitation of the extent of mass transfer from pI 6.7 to pI 5.4 (reflecting bioinactive UCRP) is accomplished by optical densitometry of the resulting isoelectric focusing gel after staining of protein with Coomassie Blue Brilliant dye.

EXAMPLES

1. Materials and Methods

Bovine ubiquitin and yeast inorganic pyrophosphatase were purchased from Sigma. In all studies the absolute concentration of ubiquitin was determined using an empirically-determined $\epsilon_{280nm}$ of 0.16 ml/mg·cm (Haas, A. L. and Wilkinson, K. D., *Prep. Biochem.* 15:49–60, 1985). Carboxypeptidase B was purchased from Boehringer Mannhelm. Recombinant ubiquitin carboxyl terminal hydrolase (L3) was a generous gift from Dr. Keith D. Wilkinson (Emory University Medical School). Human recombinant interferon bearing a C17S mutation to enhance stability (IFNβ) was supplied by Triton Biosciences. Carrier free $Na^{125}I$, $[2,8-^3H]ATP$ and $Na_4[^{32}P]PP_i$ were obtained from DuPont NEN. Ubiquitin and UCRP were labeled with $^{125}I$ by the Chloramine-T (Haas, A. L. and Rose, I. A., *Proc, Natl. Acad. Sci. USA* 78:6845–6848, 1981) and the Iodogen methods (Haas, A. L. and Bright, P. M., *J. Biol. Chem.* 262:345–351, 1987), respectively. Precast isoelectric focusing gels having a broad pH range (3.5–9.5) were obtained from Pharmacia. The ubiquitin activating enzyme (E1) was purified by modification of the published procedure (Haas, A. L. and Bright, P. M., supra, 1988) from rabbit reticulocytes, rabbit liver, and human erythrocytes.

2. Purification of Recombinant UCRP

Isolation of mature recombinant UCRP was modified from the procedure of Loeb and Haas (Loeb, K. R. and Haas, A. L., supra, 1992). All steps were conducted at 4° C. and included 5 mM $CoCl_2$ in buffers to prevent inactivation of the polypeptide by endogenous bacterial carboxypeptidase. Ten liters of *E. coli* BL21(DE3) harboring the pETUCRP expression plasmid were grown to $OD_{600nm}$ of 0.8 then harvested after a 90 minutes induction in the presence of 0.4 mM IPTG (Loeb, K. R. and Haas, A. L., supra, 1992). The centrifuged cells were resuspended in 50 mM Tris-Cl (pH 7.5) containing 5 mM $CoCl_2$ and lysed by French press. All intermediate steps were identical to those in Loeb and Haas, 1992 previously with the exception that the unadsorbed fraction from the DE-52 column was concentrated in a 200 ml Amicon cell fitted with a PM10 membrane then dialyzed against 20 mM MOPS-Cl buffer (pH 7.2) containing 5 mM $CoCl_2$. The dialyzate was adjusted to 1.6 M ammonium sulfate then applied to a 2.5×22 cm Phenyl Superose FAST column equilibrated in 20 mM MOPS-Cl (pH 7.2) containing 5 mM $CoCl_2$ and 1.6 M ammonium sulfate. Recombinant UCRP was eluted from the Phenyl Superose column as a single peak using a negative linear gradient of ammonium sulfate (5 mM/ml). Following concentration in an Amicon cell fitted with a PM10 membrane, the sample was resolved on a 2.5×36 cm preparative column of Superdex-75 equilibrated with 50 mM Tris-Cl (pH 7.5), 50 mM NaCl, and 5 mM $CoCl_2$ to remove trace high molecular weight contaminants. Fractions containing UCRP were pooled and adjusted to 1 mM DTT then dialyzed against 50 mM Tris-Cl (pH 7.5) containing 1 mM DTT. Concentration of the apparently homogeneous recombinant UCRP (>99% by SDS-PAGE followed by Coomassie Blue staining) was determined spectrophotometrically using an $\epsilon_{280}$ nm of 0.82 ml/mg·cm (Loeb, K. R. and Haas, A. L., supra, 1992). Addition of $CoCl_2$ to the buffers during purification precluded use of 1 mM DTT to eliminate dimerization of UCRP via the single cysteine residue (Knight, E., Jr., et al., supra, 1988; Loeb, K. R., *The Functional Characterization of the Ubiquitin Cross Reactive Protein, an Interferon inducible Ubiquitin Homolog*, Medical College of Wisconsin, Milwaukee, Wis., 1993). The addition of 1 mM DTT to the final dialysis step resulted in a dark brown precipitate that was removed by centrifugation. Loss of protein in the precipitate was minimal.

The ability of recombinant UCRP to substitute for ubiquitin was compared in several types of activity assays. Rates of ATP:$PP_i$ exchange were measured at 37° C. in a final volume of 50 μl containing 50 mM Tris-Cl (pH 7.6), 2 mM ATP, 10 mM $MgCl_2$, 100 μM $^{32}PP_i$ (200 cpm/pmol), 1 mM DTT, 1 pmol rabbit reticulocyte ubiquitin activating enzyme, and a range of UCRP concentrations (Haas, A. L. and Rose, I. A., supra, 1982). The incorporation of $^{32}PP_i$ into ATP was measured by adsorbing the resulting $^{32}$P-labeled ATP onto charcoal and counting the bound radioactivity by Cerenkov radiation (Haas, A. L. and Rose, I. A., supra, 1982). Nonspecifically-bound $^{32}PP_i$ was corrected by subtracting radioactivity in control incubations conducted in the absence of added E1 (Haas, A. L. and Rose, I. A., supra, 1982). Independent control experiments (not shown) demonstrated that residual $CoCl_2$ remaining in the UCRP did not affect the rate of E1-catalyzed ATP:$PP_i$ exchange supported by equivalent concentrations of ubiquitin.

3. Cell Culture and Preparation of Extracts

Confluent monolayer cultures of A549 human lung carcinoma cells were grown in Dulbecco's modified Eagle's medium supplemented with 10% (v/v) heat-inactivated fetal bovine serum. Cultures were maintained at 37° C. in a humidified 5% $CO_2$ atmosphere. Cultures of A549 cells were induced by adding IFNβ to a final concentration of 1000 IU/ml (Loeb, K. R. and Haas, A. L., supra, 1992). Following 24 hours induction, cells were rinsed twice with PBS then harvested by scraping directly into 50 mM Tris-Cl (pH 7.6) containing 2 mMATP, 10 mM $MgCl_2$, and 1 mM DTT (100 μl/100 mm plate). The cells were then briefly sonicated and the extracts used without further fractionation.

4. Bioreactive UCRP Supports E1-Catalyzed ATP:$PP_i$ Exchange

One possible assay for the improved bioactive characteristic of UCRP is the measurement of the ability of a UCRP preparation to support ATP:$PP_i$ exchange by ubiquitin activating enzyme. An obligatory step in the conjugation of ubiquitin, and presumably UCRP, requires activation of the polypeptide carboxyl terminus by E1 (Haas, A. L., et al., supra, 1982). Recombinant intact UCRP was tested below for its ability to support ATP:$PP_i$ exchange catalyzed by rabbit reticulocyte ubiquitin activating enzyme. Initial rates of ATP:$PP_i$ exchange are preferably measured at UCRP concentrations ranging from 5 to 50 μM in the presence of 20 nM E1.

The UCRP concentration dependence on the rates of isotope exchange displayed normal hyperbolic kinetics from which graphical analysis by double reciprocal plot (not shown) yielded estimates of $k_{cat}$ and $K_{1/2}$ (see TABLE I). Since these measurements were conducted in the absence of added AMP, the kinetic constants reflect step 3 of the E1 reaction involving formation of the final ternary complex (Haas, A. L. and Rose, I. A. *J. Biol. Chem.*, supra, 1982). Recombinant UCRP exhibited a $K_{1/2}$ value of 24 μM, 20-fold greater than the value of 1.2 μM reported for step 3 in the ubiquitin-supported reaction (Haas, A. L. and Rose, I. A., supra, 1982). In addition, the $k_{cat}$ for UCRP of 0.026 $s^{-1}$ is 370-fold lower than the value of 9.6 $s^{-1}$ determined for ubiquitin (Haas, A. L. and Rose, I. A., supra, 1982). Qualitatively similar results were obtained with rabbit liver E1.

TABLE I

Comparison of E1-Catalyzed ATP:$PP_i$ Exchange

| | Ubiquitin* | UCRP |
|---|---|---|
| $k_{cat}$ ($s^{-1}$) | 9.6 | 0.026 |
| $K_{1/2}$ (μM) | 1.2 | 24 |

*Values taken from (Haas, A. L., et al., J. Biol. Chem. 257:10329–10337, 1982.

Subsequent rate studies using UCRP preparations having variable amounts of intact carboxyl terminus yielded comparable values of $k_{cat}$ but different values for $K_{1/2}$ that were inversely proportional to the fraction of total UCRP possessing an intact carboxyl terminus, as judged by relative Coomassie staining intensity in the pI shift assay following incubation with carboxypeptidase B. The latter observations are consistent with the inability of des-glygly UCRP to support the E1-catalyzed reaction. The dependence of ubiquitin concentration on E1-catalyzed ATP:$PP_i$ exchange exhibits pronounced substrate inhibition at high concentrations, characteristic of the obligatory ordered addition of substrates for which ATP binds prior to ubiquitin (Haas, A. L. and Rose, I. A., supra, 1982). However, no substrate inhibition was observed at the highest concentration of UCRP tested (50 μM), presumably because this concentration remains below the zone of inhibition for the polypeptide. Insolubility of UCRP at higher concentrations prevented testing for substrate inhibition by UCRP.

5. Stoichiometry of E1-Bound UCRP Adenylate Formation

The ATP:$PP_i$ exchange reaction proceeds through a tightly E1-bound ($K_d \leq 10^{-14}$ M, (Haas, A. L. and Rose, I. A., supra, 1982; Burch, T. J. and Haas, A. L., supra, 1994) ubiquitin adenylate intermediate that is stoichiometric with the activating enzyme in the presence of inorganic pyrophosphatase (Haas, A. L., et al., supra, 1982). Therefore, the low $k_{cat}$ observed for UCRP could result in part from a stoichiometry of UCRP adenylate formation less than that found for ubiquitin adenylate. Formation of ubiquitin and UCRP adenylates were quantitated by TCA-precipitable radioactivity in the presence of [2,8-$^3$H]ATP as described in "Materials and Methods" In the presence of 1 pmol of E1 and inorganic pyrophosphatase, ubiquitin rapidly formed an equivalent amount of ubiquitin [$^3$H]adenylate within a 1 minute incubation (not shown), as reported previously (Haas, A. L. and Rose, I. A., supra, 1982). In contrast, UCRP [$^3$H]adenylate formation was only 0.11 pmol after 5 minutes under identical conditions (not shown). The low level of UCRP [$^3$H] adenylate formation was not a kinetic effect since the amount of intermediate was unaltered by longer incubation. Subsequent kinetic studies demonstrated that UCRP [$^3$H] adenylate formation was first order with a rate constant of 0.42 $min^{-1}$. Since ubiquitin [$^3$H]adenylate formation is complete within 1 minute, an analogous rate constant for formation of this intermediate could not be determined, as has been noted previously (Burch, T. J. and Haas, A. L., supra, 1994); however, a lower limit of ≧6 min$^{-1}$ could be estimated based on the limit of detection for this assay (Burch, T. J. and Haas, A. L., supra, 1994). Therefore, the substoichiometric formation of UCRP [$^3$H]adenylate probably results in part from a lower rate of intermediate formation.

Recent studies by Burch and Haas have shown that mutagenesis of specific ubiquitin residues sufficiently compromises binding of the resulting adenylate within the E1 active site to allow dissociation of the intermediate (Burch, T. J. and Haas, A. L., supra, 1994). The free but not the bound pool of ubiquitin [$^3$H]adenylate is sensitive to cleavage by ubiquitin carboxyl terminal hydrolase (Burch, T. J. and Haas, A. L., supra, 1994; Pickart, C. M. and Rose, I. A., J. Biol. Chem. 260:7903–7910, 1985). Considering the anticipated structural differences between ubiquitin and UCRP, the UCRP [$^3$H]adenylate measured by TCA precipitation could represent a similar equilibrium between bound and free forms since this method is otherwise unable to distinguish between the pools, as has been discussed previously (Burch, T. J. and Haas, A. L., supra, 1994). The amount of UCRP [$^3$H]adenylate formed was unaffected by incubation in the presence of 0.4 IU/ml of recombinant ubiquitin carboxyl terminal hydrolase, precluding the existence of a free pool of intermediate. Separate control studies demonstrated that the UCRP [$^3$H]adenylate was completely cleaved by the hydrolase if the intermediate was first dissociated from E1 by TCA precipitation then resolubilized in the presence of 0.2 M triethanolamine-Cl (pH 8.0), not shown. These results indicate that nonconservative sequence differences between ubiquitin and the carboxyl terminal ubiquitin-like domain of UCRP affects the equilibrium formation of UCRP adenylate but not the tight binding characteristic of this intermediate.

6. In vitro Conjugation of UCRP to Cellular Proteins

Previous reports by Loeb and Haas have indirectly demonstrated the presence of UCRP conjugates within interferon-responsive cultured cells (Loeb, K. R. and Haas, A. L., supra, 1992; Loeb, K. R. and Haas, A. L., supra, 1994). The subsequent inability to show in vitro conjugation of radioiodinated recombinant UCRP in cell culture extracts is accounted for by the proteolytic inactivation of the polypeptide during isolation. We have demonstrated through autoradiographic analysis that intact $^{125}$I-UCRP isolated in the presence of CoCl$_2$ shows measurable rates of in vitro conjugation when added to extracts obtained from uninduced and interferon-β treated human A549 lung carcinoma cells.

For the incubations, $^{125}$I-UCRP was added to a final concentration 50-fold greater than that of endogenous UCRP present in the extracts to obviate effects of isotope dilution. Radioiodinated UCRP exhibits a low but measurable rate of conjugation to cellular proteins present in extracts obtained from uninduced cells (−IFN) after 90 minutes incubation. The rate of $^{125}$I-UCRP conjugation is significantly greater in extracts from parallel A549 cultures induced for 24 hours in the presence of 1000 IU/ml of interferon-β (+IFN). Enhanced in vitro conjugation of $^{125}$I-UCRP agrees with the previous results demonstrating the late induction of UCRP conjugating activity by IFN-β (Loeb, K. R. and Haas, A. L., supra., 1992; Loeb, K. R., supra, 1993). Conjugation of $^{125}$I-UCRP in both extracts is absolutely dependent on the presence of ATP and a creatine phosphate/creatine phosphokinase ATP regenerating system. That the conjugation of $^{125}$I-UCRP is specific for the homolog is demonstrated by the marked inhibition by isotope dilution when an excess of unlabeled UCRP (+UCRP) but not ubiquitin (+Ub) is included in parallel incubations. The latter observations suggest that conjugation of UCRP and ubiquitin proceed through distinct ligation pathways, consistent with the earlier conclusion that UCRP activation is unlikely to require ubiquitin activating enzyme.

The significant number of additional low molecular weight radiolabeled bands obvious at 0 minutes and persisting after 90 minutes incubation is not due to contaminating proteins present in the recombinant UCRP preparation since the polypeptide was >99% pure but, rather, results from covalent aggregation of the radioiodinated polypeptide during the labeling reaction (Farrell, P. J., et al., Nature 279:523–525, 1979). Preliminary studies indicate that this aggregation results in part from disulfide dimerization of UCRP through the single cysteine residue present in the sequence under the non-reducing conditions required for radioiodination (Farrell, P. J., et al., supra, 1979).

7. Production of UCRP-R

A second method of producing bioactive UCRP involves the expression of a new recombinant protein UCRP-R in which an additional arginine amino acid has been added to the carboxyl terminal glycine of mature human UCRP. The arginine carboxyl terminal capping residue present on UCRP-R blocks the action of the endogenous bacterial carboxypeptidase responsible for inactivating UCRP by cleavage of the glycine dipeptide. Expression of UCRP-R can be used in place of purification of UCRP in the presence of cobalt as a method of producing bioactive protein.

An arginine codon was genetically inserted into the pETUCRP expression plasmid between the codon for the carboxyl terminal glycine of the UCRP coding sequence and the STOP codon to generate the unique pETUCRP-R expression plasmid. The correct nucleotide sequence for the new coding region was confirmed by dideoxy DNA sequencing.

The unique UCRP-R protein is expressed in BL21 (DE3) cells by the method used for UCRP. The cells are lysed and the UCRP-R protein is purified identically to that of UCRP with the exception that cobalt and other metals are excluded from the buffers. The presence of the extra +1 charge imparted by the arginine capping residue allows insertion of an additional step after the Phenyl Superose step which yields a higher resolution of UCRP-R from minor contaminating proteins present at <0.1% by weight of the original UCRP protein at the final stage of purification. Fractions from the Phenyl Superose column containing UCRP-R are pooled and dialyzed against distilled water then adjusted to 10 mM sodium citrate buffer (pH 6.0). The sample is applied to an HR 10/10 Mono S FPLC column equilibrated with 10 mM sodium citrate (pH 6.0) and isocratically eluted at 8 column volumes at a flow rate of 2 ml/min. Fractions containg UCRP-R are then pooled and applied directly to the Superdex-75 column as published.

The arginine capping residue is removed from purified UCRP-R by incubating the UCRP-R protein at 37° C. in 50 Tris-Cl (pH 7.5) in the presence of sufficient carboxypeptidase B to remove the arginine residue within 15 minutes. The reaction solution is then applied to a HR 5/10 Mono Q FPLC column equilibrated in 50 mM Tris-Cl (pH 7.5). Free intact UCRP resulting from removal of the arginine cap passes through the column without binding while the carboxypeptidase B is bound to the column.

The intact UCRP is assayed for protein content spectrophotometrically and for the presence of the carboxyl terminal glycine residues by the pI shift assay and the ability to support E1-catalyzed ATP:PP$_i$ exchange. The UCRP generated from UCRP-R has consistently been found to be 100% in the bioactive form as judged by the absence of a pI shift and the K$_{1/2}$ for ATP:PP$_i$ exchange of 24 μM.

I claim:

1. A method of preparing recombinant ubiquitin cross-reactive protein (UCRP) comprising the steps of purifying UCRP from a bacterial host cell in the presence of cobalt, wherein the cobalt prevents proteolytic inactivation of UCRP occurring by cleavage of the UCRP carboxyl terminal glycine dipeptide and wherein the host cell is not subjected to temperature at or above 42° C.

2. The method of claim 1 wherein the cobalt is in the form of CoCl$_2$.

3. The method of claim 1 wherein the UCRP is purified from *E. coli* cells containing pETUCRP.

4. The method of claim 2 wherein the concentration of CoCl$_2$ is between 3 mM and 10 mM.

5. The method of claim 4 wherein the concentration of COCl$_2$ is approximately 5 mM.

6. The method of claim 1 additionally comprising the step of analyzing the purified UCRP by measuring E1-catalyzed ATP:PP$_i$ exchange.

7. The method of claim 1 additionally comprising the step of analyzing the purified UCRP by exposing the UCRP to carboxypeptidase B and determining whether the UCRP has a shifted pI value, wherein the pI shift is 6.7 to 5.4.

8. A method of preparing recombinant ubiquitin cross-reactive protein (UCRP) comprising the steps of (a) expressing UCRP-R (UCRP-arginine) or UCRP-K (UCRP-lysine) in a bacterial host cell from a genetic construct encoding UCRP with an additional lysine or arginine residue at the UCRP carboxy terminal, wherein the construct is not heat-inducible, (b) purifying the expressed UCRP-R or UCRP-K, and (c) removing the additional lysine or arginine residue, wherein UCRP is obtained.

9. The method of claim 8 wherein UCRP-R (UCRP-arginine) is formed in step (a).

10. The method of claim 9 wherein the residue is removed with carboxypeptidase B.

* * * * *